(12) United States Patent
Chen et al.

(10) Patent No.: US 6,309,363 B1
(45) Date of Patent: Oct. 30, 2001

(54) DEVICE AND METHOD FOR CHARACTERIZATION OF THE SKIN BY TRIBOMETRY

(75) Inventors: Yan-Ming Chen; Jean-Claude Pavy, both of Senlis (FR)

(73) Assignee: Centre Technique des Industries Mecaniques, Senlis (FR)

( * ) Notice: Subject to any disclaimer, the term of this patent is extended or adjusted under 35 U.S.C. 154(b) by 0 days.

(21) Appl. No.: 09/522,888

(22) Filed: Mar. 10, 2000

(30) Foreign Application Priority Data

Mar. 11, 1999 (FR) .................................................. 99 03010

(51) Int. Cl.[7] ............................ A61B 5/103; A61B 5/117
(52) U.S. Cl. .................................................................. 600/587
(58) Field of Search ....................................... 600/587, 300

(56) References Cited

U.S. PATENT DOCUMENTS 4,206,769   6/1980   Dikstein .

FOREIGN PATENT DOCUMENTS 0 836 831   4/1998   (EP) .
2 749 793   12/1997   (FR) .

OTHER PUBLICATIONS

Odman, S., "Potential and Impedance Variations Following Skin Deformation," Medical & Biological Engineering & Computing, 19:271–277(1981).

Primary Examiner—Eric F. Winakur
Assistant Examiner—Brian Szmal
(74) Attorney, Agent, or Firm—Hoffman & Baron, LLP

(57) ABSTRACT

This device for characterization of the human skin consists of a tribometer 2,5,7,8 comprising a measuring arm 1 at the first end of which are mounted a measuring tip and a measuring sensor 3 capable of measuring a frictional force being exerted on the tip, and the second end of which is mounted in a support 2 enabling linear movement of the first end. An amplifier 7 and treatment means 8 and signal visualization means 9 are associated with the sensor.

9 Claims, 2 Drawing Sheets

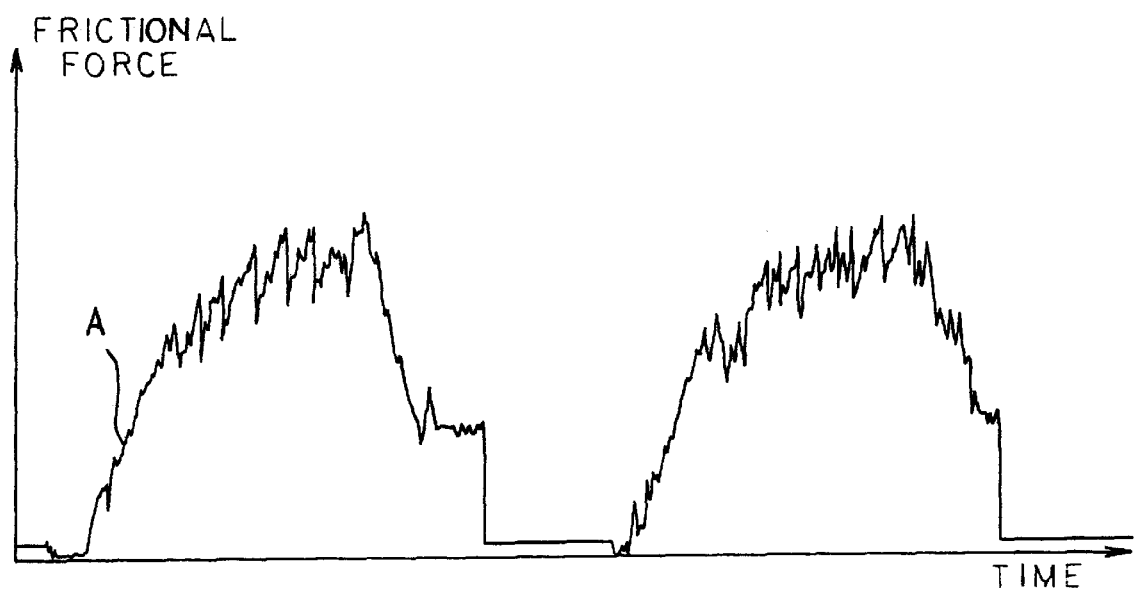
FIG_4
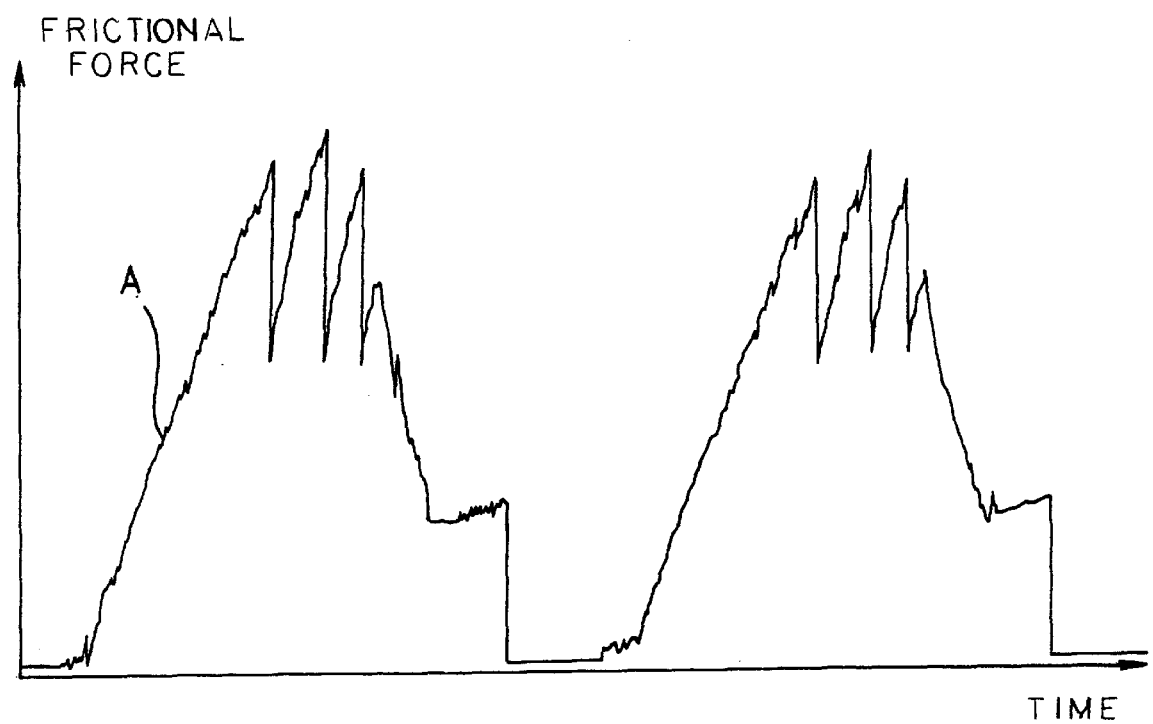
FIG_5

DEVICE AND METHOD FOR CHARACTERIZATION OF THE SKIN BY TRIBOMETRY

BACKGROUND OF THE INVENTION

1. Field of the Invention

The present invention concerns the characterization of human skin.

2. Description of the Prior Art

Numerous methods exist for attempting to characterize human skin by measuring certain properties such as elasticity, compressibility, hygrometry etc. For example, the document U.S. Pat. No. 4,206,769 A describes a probe for measuring such properties.

Also known from the document FR 2,749,793 is an electric razor that includes an integrated friction sensor, continuously measuring the degree of friction that appears between the skin and the razor grids. This result is exploited to modify the level of shaving, but not at all for characterizing the human skin.

However, these methods most often conceived for limited applications in cosmetics are aware of only certain aspects of the skin. The goal of the invention is to explore another method of characterizing the skin.

SUMMARY OF THE INVENTION

This goal is reached according to the invention by a device for characterization of the human skin, characterized in that it comprises a tribometer, that is, an apparatus for measuring the frictional force between two antagonistic surfaces, and by the associated procedure, which comprises measuring by means of a tribometer the frictional force between the skin and a measuring tip moving on the surface of the skin. The speed of movement is preferably between 0.1 mm/min and 100 mm/min.

Advantageously, the tribometer comprises a measuring arm at a first end of which are mounted a measuring tip and measuring sensor capable of measuring a frictional force being exerted on the tip, and the second end of which is mounted in a support enabling linear movement of the first end.

Advantageously, the first end comprises an articulated terminal shaft, preferably according to at least two nonparallel axes, enabling the explored surface of the skin of a subject to be followed freely with the tip.

Advantageously, the arm comprises at least a weight that is adjustable, for example, by means of weights that are added at will, and/or sliding weights, allowing a load to be exerted, preferably between 0.1 N and 10 N.

Advantageously, the measuring tip has a hemispherical end with a radius, for example, between 5 and 200 mm.

Preferentially, the measuring tip is covered with a fabric, for example by gluing, especially with a self-adhesive fabric. This fabric may be formed from any type of woven material based on organic fibers of plant, animal, mineral or synthetic origin. A woven material has the advantage of not having a great difference between the coefficient of static friction and the coefficient of dynamic friction.

Downstream of the sensor the device comprises an amplifier that receives signals from the sensor, especially load and frictional force signals, and sends them on a device for visualization or archiving.

Other characteristics and advantages of the present invention will emerge from the description below of an embodiment of the invention illustrated in the attached drawings in which:

BRIEF DESCRIPTION OF THE DRAWINGS

FIGS. 4 and 5 are two graphs of frictional force obtained during tests on two different subjects.

DETAILED DESCRIPTION OF THE INVENTION

Figure 1:
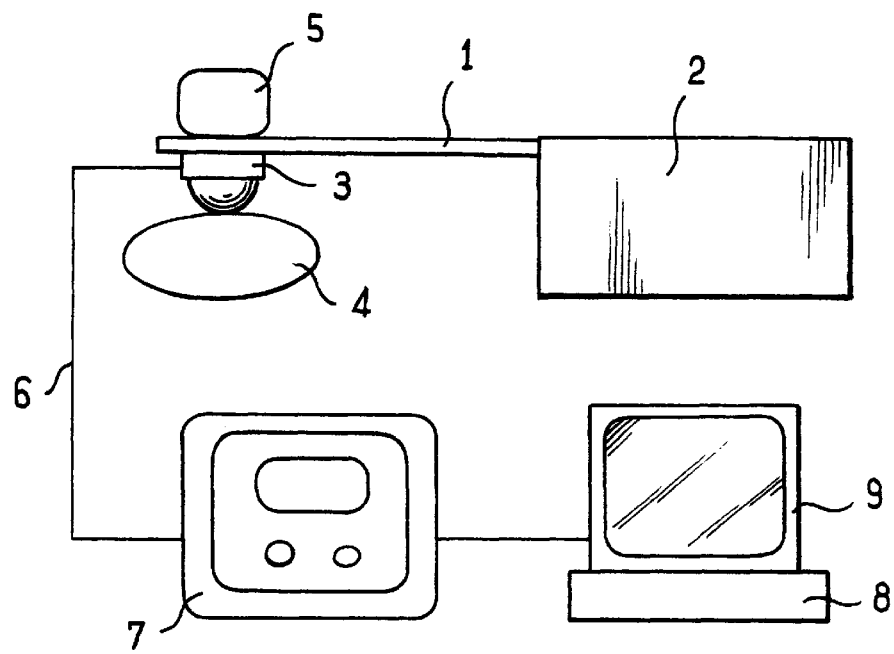
FIG. 1 is a diagram of the device in conformance with the invention

The device of the invention essentially comprises a measuring arm 1 supported by a support 2 with motor enabling linear movement to be achieved, the course of which is of adjustable length. The measuring arm 1 includes at its end a three-dimensional piezoelectric force sensor 3 represented positioned with a measuring tip on arm 4 of a person, under an adjustable load 5. A line 6 sends the signals emitted by the sensor 3, representative of the load and the frictional force, towards an amplifier 7, then towards a microcomputer 8 with a view to exploitation, archiving and/or posting of the results (on screen 9, on a plotter etc.).

Figure 2:
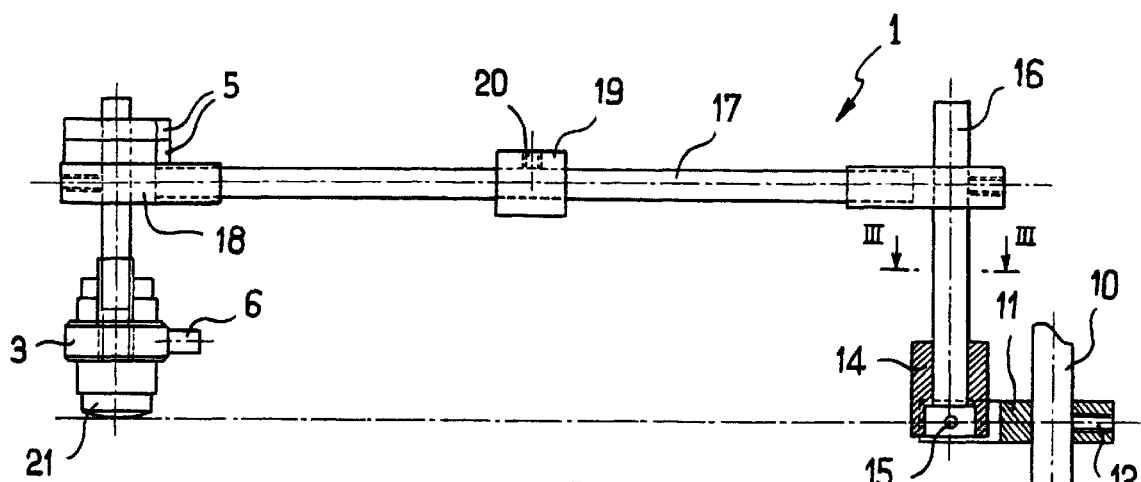
FIG. 2 is a side view of the detail of making the measuring arm of the device of FIG. 3 is a sectional view III—III of the arm of FIG. 2
Figure 3:
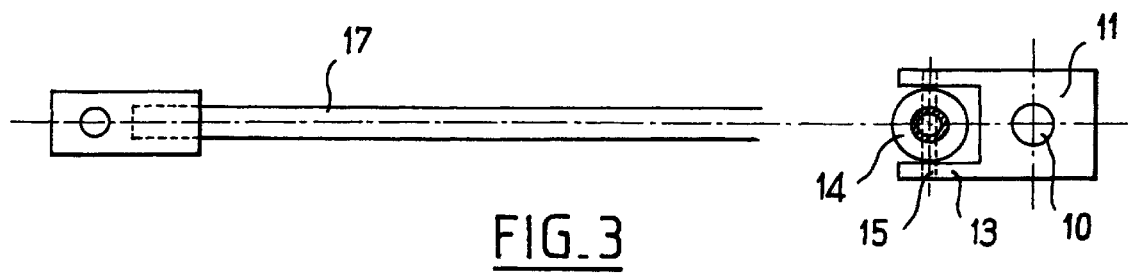

FIGS. 2 and 3 show the detail of an embodiment of the end of the measuring arm 1. It comprises a first part terminated by a vertical pin 10, this part being supported by support 2 so as to be mobile during translation. On this pin 10, a fork joint 11 is attached through a screw 12 at an adjustable height. In the fork 13 of the fork joint 11, a base 14 is attached so that it pivots due to shaft 15, the base 14 supporting a turning pin 16 on which is attached at an adjustable height a rod 17 horizontal overall (but may be inclined as a result of the hinge of base 14). At its end, rod 17 supports a fitting 18 on which are mounted on one side sensor 3 and on the other side a fixed load 5, for example, of 20 g. Along rod 17, a mobile load, for example, also of 20 g, may slide and be kept in position by a screw 20. The whole unit is very light (less than 150 g in an embodiment). The sensor 3 used in the embodiment is a Kistler 9251A sensor; the measuring tip 21 is cylindrical with a hemispherical end (radius of 30 mm) and comes approximately to the level of the hinge pin 15 when rod 17 is horizontal. The advance speed of the motorized support 2 is, for example, 0.05 mm/sec for approximately 40 sec.

Tests have been carried out on the forearm of subjects. For the tests, tip 21 of the sensor was covered with a piece of glued cloth acting as antagonistic surface to the arm of the subject. The signal of the frictional force according to time (and therefore of the movement of the tip on the surface of the skin) is recorded on graphs analogous to those of FIGS. 4 and 5

It has been noted that the variation of the frictional force during the test is very variable according to the person, but very reproducible for a given person, and therefore characteristic of that person. Moreover, it has been found that the evolution of the frictional force is identical when the same test is carried out on the same person two days after the first test.

The first part of the signal (A on FIGS. 4 and 5) of the frictional force corresponds to elastic deformation of the structural unit formed especially of skin and muscles. The coefficient of static friction during the first movement between the skin and the measuring tip is noted. The result of the signal contains the coefficient of static friction and the coefficient of dynamic friction at the same time.

The amplitude and frequency of the signal, which are very personalized, may contain information connected with the person, the texture of the skin, to the hair, to fat, to the shear behavior of the skin and the muscular structure.

The device and the procedure of the invention especially may enable the detection of anomalies of the usual profile of a subject (especially following cutaneous diseases not necessarily detectable with the naked eye) or the return to a usual profile, and give comparable indications to those an experienced physician may infer when he passes his hand over the skin of a patient.

What is claimed is:

1. A device for characterization of human skin comprising:
    a tribometer having a measuring tip arranged to be moved on the surface of the skin for measuring a characteristic of the skin; and
    an output device for receiving and analyzing the measurement information from the tribometer.

2. The device according to claim 1, wherein the tribometer comprises a measuring arm having a first end and a second end, the first end having mounted thereon the measuring tip and a measuring sensor for measuring a frictional force being exerted on the tip and the second end being mounted in a support for enabling linear movement of the first end.

3. The device according to claim 2, wherein the first end of the measuring arm comprises an articulated terminal rod.

4. The device according to claim 3, wherein the articulated terminal rod is articulated according to at least two nonparallel axes.

5. The device according to claim 2, wherein the measuring arm comprises at least one adjustable weight.

6. The device according to claim 1, wherein the measuring tip has a hemispherical end.

7. The device according to claim 1, wherein the measuring tip is covered with a cloth.

8. The device according to claim 2, wherein the measuring sensor sends signals to the output device for analyzing the signals.

9. A method for characterizing the human skin comprising the steps of:
    measuring by means of a tribometer the frictional force between the skin and a measuring tip being moved on the surface of the skin; and
    sending the measurement information to an output device for analysis.

* * * * *